United States Patent [19]
Kleiman

[11] 3,957,892
[45] May 18, 1976

[54] STABILIZED VINYLIDENE HALIDE

[75] Inventor: Joseph P. Kleiman, Birmingham, Mich.

[73] Assignee: Ethyl Corporation, Richmond, Va.

[22] Filed: Dec. 13, 1974

[21] Appl. No.: 532,710

Related U.S. Application Data

[63] Continuation-in-part of Ser. No. 363,071, May 23, 1973, Pat. No. 3,868,426.

[52] U.S. Cl.......................................... 260/652.5 R
[51] Int. Cl.$^2$.......................................... C07C 17/42
[58] Field of Search............... 260/652.5 R, 652.5 P

[56] References Cited
UNITED STATES PATENTS 2,616,883   11/1952   Marous........................ 260/652.5 P 3,868,426   2/1975   Kleiman ........................ 260/652.5 P

OTHER PUBLICATIONS

Def. Pub. (Werts, III) T887,010 Published 6-1-71.

Primary Examiner—Delbert E. Gantz
Assistant Examiner—Joseph A. Boska
Attorney, Agent, or Firm—Donald L. Johnson; John F. Sieberth; Robert A. Linn

[57] ABSTRACT

Vinylidene bromide and vinylidene chlorobromide are stabilized by a conjugated butadiene such as isoprene used in conjunction with a phenolic composition such as butylated hydroxyanisole.

11 Claims, No Drawings

STABILIZED VINYLIDENE HALIDE

CROSS REFERENCE TO RELATED APPLICATION

This is a continuation-in-part of application, Ser. No. 363,071, filed May 23, 1973, now U.S. Pat. No. 3,868,426.

BACKGROUND OF THE INVENTION

British Pat. No. 1,139,854 teaches stabilized vinylidene bromide with styrene.

Various other substances are known to stabilize halogenated materials; for example, U.S. Pat. No. 3,225,108 teaches stabilization of vinyl chloride with phenol and derivatives; confer columns 1–15. U.S. Pat. No. 2,136,333 teaches stabilization of vinylidene chloride with various phenols, as does U.S. Pat. No. 2,121,010. U.S. Pat. No. 2,810,765 teaches stabilization of vinyl chloride with a thiophenol. U.S. Pat. No. 3,062,900 teaches stabilization of vinyl and vinylidene chloride with p-methoxyphenol. Jolls, Z. E., *Bromine and Its Compounds*, Academic Press, New York, N.Y. 1966, page 625, teaches stabilization of vinylidene bromide with hydroquinone or metallic copper. Defensive Publication No. T887,010 teaches stabilization of vinylidene chloride with alkyl ethers of 2,6-di-tert-butylhydroquinone.

SUMMARY OF THE INVENTION

This invention pertains to stabilized vinylidene bromide and chlorobromide. The invention entails stabilization of these substances with a stabilizing amount of a mixture of a conjugated butadiene and a phenol.

Preferably the conjugated diene has from 4 to about 12 carbon atoms and the formula

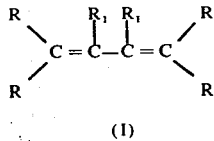

(I)

wherein R is selected from the class consisting of hydrogen and hydrocarbyl radicals of up to about 8 carbons, and $R_1$ is selected from the class consisting of hydrogen, chlorine, bromine, and alkyl radicals of up to about 8 carbon atoms, such that no more than one $R_1$ is halogen, said hydrocarbyl radicals being free from aliphatic unsubstitution.

Preferably the phenol has up to about 16 carbons and the formula

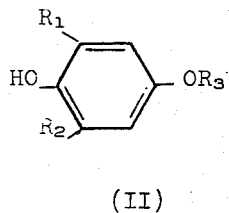

(II)

wherein $R_1$ is an α-branched alkyl group of 3 to about 8 carbons, $R_2$ is hydrogen or alkyl group containing up to about 8 carbons and $R_3$ is hydrogen or a hydrocarbyl radical of up to about 8 carbon atoms.

In a more preferred embodiment, the conjugated butadiene is selected from isoprene, chloroprene and 1,3-butadiene. In another preferred embodiment the phenolic material is butylated hydroxyanisole.

In a highly preferred embodiment, the stabilizing composition comprises a mixture of butylated hydroxyanisole and a diene selected from isoprene, chloroprene, and 1,3-butadiene, most preferably isoprene.

DESCRIPTION OF PREFERRED EMBODIMENTS

This invention pertains to stabilization of vinylidene bromide and vinylidene chlorobromide, brominated hydrocarbons which are susceptible to deterioration upon standing. Generally, any butadiene compound which stabilizes vinylidene bromide or vinylidene chlorobromide can be used in this invention. The preferred additives are soluble in the amounts employed. More preferably, the additives should have up to about 12 carbons and should not react or otherwise decompose, whereby the stabilization is diminished to an undesirable extent during the period for which stabilization is desired.

Below are listed non-limiting examples of hydrocarbyl groups which may be present in the above general formula I as groups $R - R_1$.

Examples of alkyl groups represented by the groups $R - R_1$ in the above general formula are methyl, ethyl, n-propyl, isopropyl, n-butyl, isobutyl, sec-butyl, tert-butyl, n-amyl, and the various positional isomers thereof, and likewise the corresponding straight and branched chain isomers of hexyl, heptyl, octyl, nonyl, decyl, undecyl, dodecyl, and the like.

When said groups $R - R_1$ are cycloalkyl groups, they may be cyclopropyl, cyclobutyl, cyclopentyl, cyclohexyl, cycloheptyl, cyclooctyl, cyclononyl, cyclodecyl, cycloundecyl, cyclododecyl, and the like. They may also be such cycloaliphatic groups as α-cyclopropylethyl, α-cyclobutylpropyl, and similar alkyl derivatives of the higher cycloalkyls.

When the groups $R - R_1$ are aralkyl groups, they may be benzyl, phenylethyl, 1-phenylpropyl, 2-phenylpropyl, 3-phenylpropyl, the 1- and 2-isomers of phenylisopropyl, the 1-, 3-isomers of phenylbutyl, and the like.

One of the $R_1$ groups may contain a non-hydrocarbon substituent such as —Cl or —Br, preferably chlorine.

Preferred stabilizers of this invention are isoprene, chloroprene, and 1,3-butadiene.

Although one diene can be used, the halogenated hydrocarbon can be stabilized with mixtures of butadiene compounds of the type described above. Two, three or more butadiene compounds can be used as the stabilizer additive. A suitable mixture is isoprene and chloroprene.

Generally, any phenol which stabilizes vinylidene bromide, or vinylidene chlorobromide can be used in this invention. The preferred additives are soluble in the amounts employed. As with the dienes, the phenols should not react or otherwise decompose, whereby the stabilization is diminished to an undesirable extent during the period for which stabilization is desired.

The radicals mentioned above which have up to about 8 carbon atoms are non-limiting examples of hydrocarbyl radicals which can be present as $R_2$ or $R_3$ in general formula II above.

In α-branched alkyl radicals in the phenolic compounds, the carbon atom in the position adjacent to the benzene ring has a side chain branch containing at least one carbon atom. Examples of such radicals are isopropyl, sec-butyl, sec-amyl, sec-isoamyl, tert-amyl, sec-hexyls, tert-hexyls, sec-dodecyls, cyclopropyl, cyclopentyl, cyclohexyl, α-methylbenzyl, α,α-dimethylbenzyl, 4-isopropyl-α,α-dimethylbenzyl, and the like.

In the above phenolic materials, $R_2$–$R_3$ may also be alkenyl groups such as ethenyl, 1-propenyl, 2-propenyl, isopropenyl, 1-butenyl, 3-butenyl and the corresponding branched chain isomers thereof as, for example, 1-isobutenyl, 2-isobutenyl, 2-sec-butenyl, including 1-methylene-2-propenyl, and the various isomers of pentenyl, hexenyl, heptenyl, octenyl, nonenyl-decenyl, undecenyl, and dodecenyl, including 3,3-dimethyl-1-butentyl, 2,3-dimethyl-1-butenyl, 2,3-dimethyl-2-dimethyl-3-butenyl, 1-methyl-1-ethyl-2-propenyl, and the like.

When $R_2$–$R_3$ in the phenolic compound are alkaryl groups, they may be 2,3-xylyl, 2,3-xylyl, 2,5-xylyl, 2,6-xylyl, 3,4-xylyl, 3,5-xylyl, o,m, and p-cumenyl, mesityl, o,m, and p-ethylphenyl, 2-methyl-naphthyl, 3-methyl-1-naphthyl, 4-methyl-1-naphthyl, 5-methyl-2-naphthyl, 6-methyl-3-naphthyl, 7-methyl-1-naphthyl, 8-methyl-4-naphthyl, 1-ethyl-2-naphthyl, and its various positional isomers, and the like.

Examples of aryl groups which may be present as $R_2$–$R_3$ in the phenolic compounds are phenyl, naphthyl, and the like.

Such compounds suggest the use of stable, related compounds in which one or more of the groups $R_2$–$R_3$ contain a non-hydrocarbon substituent such as —Cl, or —Br.

Although one phenol can be used, vinylidene bromide or vinylidene chlorobromide can be stabilized with mixtures of phenols of the type described above together with one or more butadienes. Two, three or more phenol compounds can be used in the stabilizer additive. A suitable phenol mixture is a mixture of the ethyl and n-butyl ethers of 2,6-di-tert-butylphenol illustrated by the above general formula.

As mentioned above, a preferred embodiment of this invention is vinylidene bromide stabilized with butylated hydroxyanisole (BHA), a mixture of the 2-, and 3-tert-butyl derivatives of p-hydroxyanisole. The use of BHA suggests the other additives of this invention need not be pure.

Also, to the extent the 3-tert-butylhydroxyanisole derivative adds to the stabilization, this suggests use of such 3-isomers with the diene stabilizers of this invention.

Furthermore, this invention includes stabilization of vinylidene bromide and vinylidene chlorobromide with a stabilizer mixture comprising a diene and a compound having the formula

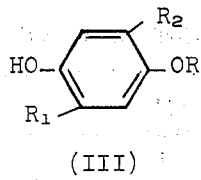

(III)

wherein $R_1$–$R_3$ have the same significance as above.

A stabilizing amount of stabilizer is employed. The amount used can be varied and is dependent, at least to some extent, on the activity of the stabilizer. By tests, such as described below, stabilization achieved by various additive concentrations can be observed. With the data obtained, a skilled practitioner can select the desired concentration. In general, the amount of diene stabilizer is less than 20 weight per cent. A preferred concentration range is from about 0.5 to about 15 weight per cent; most preferably from about 1 to about 10 per cent by weight. In general, the amount of phenolic compound is less than one weight per cent, usually lss than 0.1 per cent and preferably from 500 to 10,000 ppm by weight.

The stabilizer additive and halogenated material to be stabilized can be admixed in any known manner.

EXAMPLE

Storage stability tests were carried out in the following manner. The vinylidene bromide was distilled onto the stabilizer system in a nitrogen atmosphere. The sampls were stored in a Schlenk tube at 110° in the dark in a nitrogen atmosphere. The materials were sampled each week and the weight per cent non-volatiles and the methanol insolubles were determined. A material was failed when solid formation was noted.

The resuls are summarized in Table 1 (Weight per cent Non-Volatiles) and Table 2 (Methanol Insolubles).

TABLE 1

| Stabilizer | Vinylidene Bromide Storage Stability Test - Wt. per cent Non-Volatiles Weeks | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Isoprene (0.5 per cent)BHA (1000 ppm) | 0.2 | — | 0.1 | 0.1 | 0.1 | 0.1 | 0.1 | 0.1 | — | 0.2 | — | 0.2 | |
| Isoprene (1 per cent)BHA (1000 ppm) | 0.1 | — | 0.1 | 0.1 | 0.2 | 0.2 | 0.1 | 0.1 | — | 0.2 | — | 0.45 | |

TABLE 2

| Stabilizer | Vinylidene Bromide Storage Stability Test - Wt. per cent Methanol Insolubles Weeks | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Isoprene (0.5 per cent) BHA (1000 ppm) | 0.1 | 0.1 | 0.04 | 0.04 | 0.01 | 0.04 | 0.0 | 0.0 | — | 0.0 | — | 0.1 | |
| Isoprene (1 per cent) BHA | | | | | | | | | | | | | |

TABLE 2-continued

| Stabilizer | Vinylidene Bromide Storage Stability Test - Wt. per cent Methanol Insolubles Weeks | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 | 13 |
| (1000 ppm) | 0.1 | 0.1 | 0.02 | 0.04 | 0.01 | 0.03 | 0.0 | 0.0 | — | 0.0 | — | 0.1 | |

The above results are in contrast to unstabilized vinylidene bromide which starts polymerizing in a few minutes while under nitrogen and cooled with an ice bath.

Vinylidene chlorobromide can be stabilized similarly using BHA and isoprene in the concentrations used in the above examples.

Likewise, vinylidene chlorobromide and vinylidene bromide can be stabilized with mixtures of 500 to 10,000 ppm by weight of a phenolic material admixed with from 1 to 10 weight per cent of a diene when the phenolic material is selected from butylated hydroxyanisole, (3-methyl-5-isopropyl-4-hydroxyphenyl) (methyl) ether, (3-methyl-5-tert-butyl-4-hydroxyphenyl) (ethyl) ether, (3-ethyl-5-tert-amyl-4-hydroxyphenyl) (isopropyl) ether, (3-methyl-5-(2-heptyl)-4-hydroxyphenyl) (butyl) ether, (3-ethyl-5-(1,1,3,3-tetramethyl-butyl)-4-hydroxyphenyl) (dodecyl) ether, (3,5-diisopropyl-4-hydroxyphenyl) (cyclohexyl) ether, (3,5-di-tert-butyl-4-hydroxyphenyl) (p-ethylcyclohexyl) ether, (3-isopropyl-5-tert-4-hydroxyphenyl) (benzyl) ether, (3-methyl-5-tert-amyl-4-hydroxyphenyl) (p-methylbenzyl) ether, (3,5-di-tert-amyl-4-hydroxyphenyl) (allyl) ether, (3,5-diisopropyl-4-hydroxyphenyl) (7-octenyl) ether, (3,5-di-sec-butyl-4-hydroxyphenyl) (4-hexenyl) ether, (3,5-diisopropyl-4-hydroxyphenyl) (heptyl) ether, (3,5-di-tert-butyl-4-hydroxyphenyl) (2-dodecyl) ether, (3,5-diisopropyl-4-hydroxyphenyl) (methyl) ether, (3,5-diisopropyl-4-hydroxyphenyl) (isopropyl) ether, (3,5-diisopropyl-4-hydroxyphenyl) (hexyl) ether, (3,5-di-tert-butyl-4-hydroxyphenyl) (tert-butyl) ether, (3,5-di-tert-butyl-4-hydroxybenzyl) (amyl) ether, (3-isopropyl-5-tert-butyl-4-hydroxyphenyl) (methyl) ether, (3,5-di-tert-amyl-4-hydroxybenzyl (tert-amyl) ether, (3-isopropyl-5-(1,1,2,2-tetramethylpropyl) (4-hydroxyphenyl) (ethyl) ether, and 3,5-di-(1,1,3,3-tetramethylbutyl-4-hydroxyphenyl) (1,1-dimethylbutyl) ether, and the diene is selected from chloroprene, 1,3-butadiene, 1,3-pentadiene, 1,3-dodecadiene, 1-cyclohexyl-1,2-butadiene, 2-cyclohexyl-1,3-butadiene, isoprene, and 6-phenyl-1,3-butadiene.

The stabilizer-vinylidene halide compositions of this invention can be stored under inert gases other than nitrogen; e.g. argon, neon and the like. Storage under inert gas is not critical.

This invention also extends to the stabilizing mixtures per se; that is, it includes mixtures of dienes of Formula (I) and phenolic compositions such as BHA and the compounds depicted in Formula (II) or Formula (III) when the diene and phenolic material are present in the relative amounts given by the above concentration ranges of the substances in vinylidene bromide.

I claim:

1. As a composition of matter, a vinylidene halide selected from the class consisting of vinylidene bromide and vinylidene chlorobromide stabilized with a stabilizing amount of a mixture of from about 1 to 10 weight per cent of a conjugated and from about 500 to about 10,000 ppm by weight of a phenolic material, said diene having from 4 to about 12 carbon atoms, and having the formula

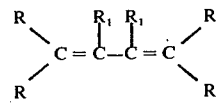

wherein R is selected from the class consisting of hydrogen and lower alkyl of up to 8 carbon atoms, and $R_1$ is selected from the class consisting of hydrogen, chlorine, bromine, and alkyl radicals of up to about 8 carbon atoms, such that no more than one $R_1$ is halogen, said phenolic material having up to about 16 carbons and the formula

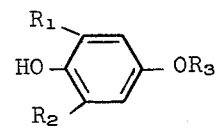

wherein $R_1$ is an α-branched alkyl group of 3 to about 8 carbons, $R_2$ is hydrogen or alkyl group containing up to about 8 carbons and $R_3$ is hydrogen or a hydrocarbyl radical of up to about 8 carbon atoms.

2. A composition of claim 1 wherein said vinylidene halide is vinylidene bromide.

3. A composition of claim 1 wherein said vinylidene halide is vinylidene chloride.

4. A composition of claim 1 wherein said diene is selected from the class consisting of isoprene, chloroprene and 1,3-butadiene.

5. A composition of claim 4 wherein said diene is isoprene.

6. A composition of claim 1 wherein $R_3$ is alkyl.

7. A composition of claim 1 wherein $R_3$ is selected from the class consisting of aryl, aralkyl and alkaryl.

8. As a composition of matter, a vinylidene halide selected from the class consisting of vinylidene bromide and vinylidene chlorobromide stabilized with a stabilizing amount of a mixture of from about 1 to about 10 weight per cent of a conjugated diene and from about 500 to about 10,000 ppm by weight of 2 and 3 -tert-butyl-4-methoxyphenol, said diene having from 4 to about 12 carbon atoms, and having the formula

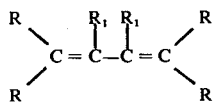

wherein R is selected from the class consisting of hydrogen and lower alkyl of up to 8 carbon atoms, and $R_1$ is selected from the class consisting of hydrogen, chlorine, bromine, and alkyl radicals of up to about 8 carbon atoms such that no more than one $R_1$ is halogen.

9. A composition of claim 8 wherein said diene is isoprene.

10. Vinylidene bromide stabilized with a stabilizing amount of from about 1 to about 10 weight per cent of isoprene and from about 500 to about 10,000 ppm by weight of 2 and 3-tert-butyl-4-hydroxyanisole.

11. Vinylidene chlorobromide stabilized with a stabilizing amount of a mixture of from about 1 to about 10 weight percent of isoprene and from about 500 to about 10,000 ppm by weight of 2 and 3-tert-butyl-4-hydroxy anisole.

* * * * *

UNITED STATES PATENT AND TRADEMARK OFFICE
CERTIFICATE OF CORRECTION

PATENT NO. : 3,957,892

DATED : May 18, 1976

INVENTOR(S) : Joseph P. Kleiman

It is certified that error appears in the above-identified patent and that said Letters Patent are hereby corrected as shown below:

Column 5, line 67, "diene" should be inserted after "conjugated"

Signed and Sealed this

Third Day of August 1976

[SEAL]

Attest:

RUTH C. MASON
*Attesting Officer*

C. MARSHALL DANN
*Commissioner of Patents and Trademarks*